United States Patent

Oka et al.

Patent Number: 5,292,950
Date of Patent: Mar. 8, 1994

[54] N,N-DIALKYLAMINOALKYL (METH) ACRYLAMIDE COMPOSITION WITH IMPROVED STORAGEABILITY

[75] Inventors: Hiroshi Oka, Hatano City; Yasutaka Doi; Takashi Maruyama, both of Yatsushiro, Japan

[73] Assignees: Kohjin Co., Ltd., Tokyo; Sumitomo Chemical Co., Ltd., Osaka, both of Japan

[21] Appl. No.: 582,186
[22] PCT Filed: Jan. 30, 1990
[86] PCT No.: PCT/JP90/00107
  § 371 Date: Nov. 13, 1990
  § 102(e) Date: Nov. 13, 1990
[87] PCT Pub. No.: WO90/08788
  PCT Pub. Date: Aug. 9, 1990

[30] Foreign Application Priority Data

Jan. 31, 1989 [JP] Japan .................................. 1-19760

[51] Int. Cl.$^5$ ............................................. C07C 237/16
[52] U.S. Cl. ........................................ 564/4; 252/403; 564/204; 564/301
[58] Field of Search .................. 564/4, 204, 301; 252/403

[56] References Cited

U.S. PATENT DOCUMENTS

| | | | |
|---|---|---|---|
| 3,642,877 | 2/1972 | Jayawant | 560/217 |
| 4,520,210 | 5/1985 | Schneider et al. | 564/204 |
| 4,745,214 | 5/1988 | Hess et al. | 564/204 |
| 4,798,889 | 1/1989 | Pluddemann et al. | 556/401 |

FOREIGN PATENT DOCUMENTS

63-270653 11/1988 Japan .

OTHER PUBLICATIONS

Nippon Zeon Co., *Chem. Abs.*, vol. 80:109060x (1974).
Sato et al., *Chem. Abs.*, vol. 77:165290x (1972)
Konecny et al., *Chem. Abs.*, vol. 86:55911d (1977).
Diaz et al., *Chem. Abs.*, vol. 97:92795s (1982).
Miller, *Chem. Abs.*, vol. 100:7384v (1984).
Zhang et al., *Chem. Abs.*, vol. 100:192330K (1984).
Miller et al., *Chem. Abs.*, vol. 101:211879K (1984).
Zhang et al., *Chem. Abs.*, vol. 103:215826e (1985).
Wang et al., *CHem. Abs.*, vol. 104:34361z (1986).
Atlantic Richfield Co., *Chem. Abs.*, vol. 105:173217r (1986).
Miller, *Chem. Abs.*, vol. 106:157000e (1987).
Miller, *Chem. Abs.*, vol. 107:40534m (1987).
Roling, *Chem. Abs.*, vol. 109:150212d (1988).

*Primary Examiner*—Glennon H. Hollrah
*Assistant Examiner*—Scott C. Rand
*Attorney, Agent, or Firm*—Oliff & Berridge

[57] ABSTRACT

A composition of an N,N-dialkylaminoalkyl(meth)acrylamide of the following formula (II), which has an improved storageability and which contains an N,N-dialkylhydroxylamine of the following formula (I) in an amount of from 10 to 10,000 ppm:

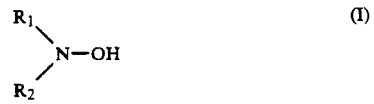

(I)

where $R_1$ and $R_2$ each independently represent an alkyl group having

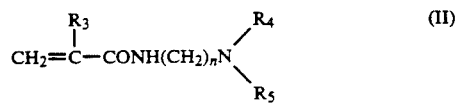
(II)

where
  $R_3$ represents a hydrogen atom or a methyl group, $R_4$ and $R_5$ each independently represent an alkyl group having from 1 to 4 carbon atoms; and
  n represents an integer of from 2 to 4.

4 Claims, No Drawings

N,N-DIALKYLAMINOALKYL (METH) ACRYLAMIDE COMPOSITION WITH IMPROVED STORAGEABILITY

TECHNICAL FIELD

The present invention relates to an N,N-dialkylaminoalkyl(meth)acrylamide composition having an extremely improved storageability.

BACKGROUND ART

An amino group-containing vinyl monomer is homopolymerized or copolymerized with other vinyl monomer(s) and is widely used as a raw material for producing various amino group-containing vinyl polymers. An amino group-containing vinyl polymer is utilized in various fields, for example, as a coagulant, a dispersing agent, an additive to a papermaking stock, a polymer for recovery of petroleum, a vehicle for coating paints, an adhesive and others.

Hitherto, as an amino group-containing vinyl monomer, an N,N-dialkylaminoalkyl(meth)acrylate has widely been utilized. Recently, however, an N,N-dialkylaminoalkyl(meth)acrylamide of the following general formula (II) has been considered important because of the excellent hydrolysis-resistance and the excellent hydrogen-bonding ability of the amido group.

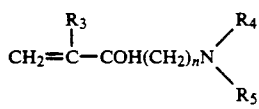

where
R$_3$ represents a hydrogen atom or a methyl group;
R$_4$ and R$_5$ independently represent an alkyl group having from 1 to 4 carbon atoms; and
n represents an integer of from 2 to 4.

However, N,N-dialkylaminoalkyl(meth)acrylamides have a problem in that the storageability thereof is poor, although they have the above-mentioned various excellent characteristics. Precisely, N,N-dialkylaminoalkyl(meth)acrylamides have a severe problem in that they are deaminated with the lapse of time under the condition of contact with oxygen to give divinyl impurities as by-products.

For instance, when N,N-dimethylaminopropylacrylamide is allowed to stand in air for a while, it gives a divinyl impurity of allylacrylamide as a by-product in an amount of several hundred ppm in one month.

Where the thus by-produced divinyl impurity-containing N,N-dialkylaminoalkyl(meth)acrylamide is polymerized, the solubility of the resulting polymer in solvents would be worsened or the viscosity of the polymer would disadvantageously increase, because of the crosslinking reaction occurring along with polymerization reaction. As a result, the polymer to be formed is to have some undesirable property which is different from the originally intended property, and such undesirable property often causes some serious problems in practical use of the polymer. In particular, when a water-soluble polymer having a high molecular weight is to be obtained, there would occur a fatal problem in that the polymer formed could not dissolve in water. Though depending upon the molecular weight of the polymer to be formed, the solubility of the polymer is generally worsened when the content of the divinyl compound impurity in the polymer is 10 ppm or more.

On the other hand, conventional N,N-dialkylaminoalkyl(meth)acrylamides color with the lapse of time in the presence of oxygen. Coloration extremely lowers the commercial value of polymer products to be obtained from the monomers. In particular, it causes a serious drawback in that the colored polymers cannot be used in a field where the appearance color of products is an important factor. Under the such situations the utilizable range of N,N-dialkylaminoalkyl(meth)acrylamides is often restricted because of the undesirable coloration of the monomers.

For overcoming the above-mentioned problems of by-production of divinyl compounds and coloration of monomers, there are known a method of polymerizing the monomers immediately after preparation or purification of the monomers, and a method of storing the monomers under the condition of an extremely low temperature. However, these methods are not industrially practicable. On the other hand, a method of minimizing the contact of an N,N-dialkylaminoalkyl(meth)acrylamide with oxygen so as to prevent by-production of divinyl impurities has been proposed (Japanese Patent Application Laid-Open No. 63-270653). However, control of the method is complicated and the method is accompanied by a dangerous possibility that the monomer will be polymerized. Therefore, the utilizable range of the method is limiting.

As mentioned above, dialkylaminoalkyl(meth)acrylamides which have an excellent storageability under a general storage condition and which are free from a problem of polymerizing are desired in this technical field.

DESCRIPTION OF THE INVENTION

In consideration of the situation as mentioned above, the present inventors earnestly studied for the purpose of obtaining a composition of an N,N-dialkylaminoalkyl(meth)acrylamide of the following formula (II), which hardly forms divinyl impurities as by-products and which hardly colors with the lapse of time, after the composition has been stored under a general storage condition or a condition where the amide is brought into contact with oxygen. As a result, they have found the fact that by-production of divinyl compounds from the amide as well as coloration of the amide can be prevented by adding a particular hydroxylamine to the N,N-dialkylaminoalkyl(meth)acrylamide. On the basis of the finding, they have achieved the present invention.

Specifically, the present invention relates to a composition of an N,N-dialkylaminoalkyl(meth)acrylamide of the following general formula (II), which has an improved storageability and which is characterized by containing an N,N-dialkylhydroxylamine in an amount of from 10 to 10,000 ppm, the hydroxylamine having a formula:

where R$_1$ and R$_2$ independently represent an alkyl group having from 1 to 4 carbon atoms. The N,N-dialkylaminoalkyl(meth)acrylamide has the formula:

where
- $R_3$ represents a hydrogen atom or a methyl group;
- $R_4$ and $R_5$ independently represent an alkyl group having from 1 to 4 carbon atoms; and
- n represents an integer of from 2 to 4.

As specific examples of N,N-dialkylhydroxylamines of the formula (I) which are used in the present invention, there are mentioned N,N-dimethylhydroxylamine, N,N-diethylhydroxylamine, N,N-diisopropylhydroxylamine, N,N-di-n-butylhydroxylamine, etc.

These N,N-dialkylhydroxylamines are generally added to N,N-dialkylaminoalkyl(meth)acrylamides in an amount of from 10 to 10,000 ppm, more preferably from 10 to 5,000 ppm. If the content of the amine of the formula (I) in the amide-containing composition is less than 10 ppm, a sufficient effect could not be attained. On the other hand, even though the content is more than 10,000 ppm, any further effect could not be obtained. Accordingly, the economical content is approximately up to 10,000 ppm, more preferably approximately up to 5,000 ppm.

As specific examples of N,N-dialkylaminoalkyl(meth)acrylamides of the formula (II) of the present invention, there are mentioned N,N-dimethylaminopropylacrylamide, N,N-dimethylaminopropylmethacrylamide, N,N-dimethylaminobutylacrylamide, N,N-dimethylaminomethacrylamide, N,N-diethylaminopropylacrylamide, N,N-diethylaminopropylmethacrylamide, etc.

It is indispensible that the N,N-dialkylaminoalkyl(meth)acrylamide composition of the present invention contain an N,N-dialkylhydroxylamine of the formula (I), and the composition may of course contain any other additives, for example, a polymerization inhibitor such as methoxyhydroquinone, and others, in addition to the amine.

BEST MODES OF CARRYING OUT THE INVENTION

Next, the present invention will be explained in more detail by way of the following examples, which, however, do not whatsoever restrict the scope of the present invention.

EXAMPLE 1

100 g of N,N-dimethylaminopropylacrylamide containing 1000 ppm of methoxyhydroquinone as a polymerization inhibitor was blended with 30 mg (300 ppm) of N,N-diethylhydroxylamine, and the resulting composition was put in an open glass container, which was stored in the dark at room temperature.

The time-dependent changes of the content of allylacrylamide, the color and the double bond percentage are shown in Table 1 below.

After being stored for 3 months, a part of the stored sample was neutralized with the same molar amount of sulfuric acid to form an aqueous 60% solution of N,N-dimethylaminopropylacrylamide sulfate.

The resulting aqueous monomer solution was sufficiently $N_2$-substituted, and 60 ppm of ammonium persulfate, 60 ppm of sodium hydrogensulfite and 100 ppm of V-50 (product of Wako Pure Chemicals Co.; 2,2'-azobis(2-aminopropane) dihydrochloride) were added to the solution, which was then subjected to adiabatic polymerization. The polymer obtained was formed into a 1N sodium nitrate solution, and the limiting viscosity thereof was obtained to be $[\eta]=7.5$.

One g of the polymer was dissolved in one liter of a pure water and filtered through a 100-mesh wire gauze. The residue was dried and the weight thereof was measured to be not more than 1 mg. The solubility of the polymer was good.

COMPARATIVE EXAMPLE 1

100 g of N,N-dimethylaminopropylacrylamide containing 1000 ppm of methoxyhydroquinone as a polymerization inhibitor was put in an open glass container, which was stored in the dark at room temperature. The time-dependent changes of the content of allylacrylamide, the appearance color and the double bond percentage are shown in Table 1 below.

After being stored for 3 months, a part of the stored sample was polymerized in the same manner as in Example 1. The polymer obtained did not dissolve in water at all but gave an insoluble gel.

EXAMPLE 2

The same process as in Example 1 was repeated, except that N,N-dimethylhydroxylamine was used as an N,N-dialkylhydroxylamine. The data of time-dependent changes are shown in Table 1.

The residue in dissolution of the polymer as obtained in the same manner as in Example 1 was not more than 1 mg, and the solubility of the polymer was good.

EXAMPLE 3

The same process as in Example 1 was repeated, except that N,N-dimethylaminopropylmethacrylamide was used as an N,N-dialkylaminoalkyl(meth)acrylamide. The data of time-dependent changes are shown in Table 1.

The limiting viscosity $[\eta]$ of the polymer as obtained in the same manner as in Example 1 was measured to be $[\eta]=4.6$. The residue in dissolution of the polymer was not more than 1 mg and the solubility of the polymer was good.

EXAMPLES 4 AND 5 AND COMPARATIVE EXAMPLE 2

N,N-diethylhydroxylamine was added to 100 g of N,N-dimethylaminopropylacrylamide, in an amount of 0 mg (0 ppm) (Comparative Example 2), 1 mg (10 ppm) (Example 4) and 500 mg (5,000 ppm) (Example 5), respectively. Each of the resulting compositions was put in an open glass container and stored in the dark at room temperature for one month. After storage, the allylamide content in the stored composition and the color of the stored composition were measured.

As a result, the allyl (meth) acrylamide content in the composition, to which 0 ppm, 10 ppm or 5,000 ppm of N,N-diethylhydroxylamine had been added, was more than 200 mg, 10 ppm and 0 ppm, respectively; and the appearance color (APHA) thereof was more than 500, 300 and 100, respectively. From the results, addition of N,N-diethylhydroxylamine was admitted effective for preventing formation of a divinyl compound which is to be a bar to polymerization of N,N-dimethylaminopropylacrylamide and also for preventing coloration of the amide.

INDUSTRIAL APPLICATION

The N,N-dialkylaminoalkyl (meth) acrylamide composition of the present invention forms an extremely reduced amount of by-product of crosslinking divinyl impurity, which has a bad influence on the properties of the polymerized polymer to be obtained from the amide by polymerization, even when it is stored in a general condition where it is brought into contact with oxygen. Additionally, coloration of the composition may noticeably be retarded during storage under such a general condition.

Moreover, the composition may directly be applied to polymerization where a general radical polymerization initiator is used, without having any bad influence thereon.

Accordingly, since the drawback of the conventional N,N-dialkylaminoalkyl(meth)acrylamide is overcome by the present invention, the range of the use of the monomer is noticeably enlarged and therefore preparation of new amino group-containing polymers which have unknown characteristics is possible from the composition of the present invention.

TABLE 1

| Item | Period (month) | Comparative Example 1 | Example 1 | Example 2 | Example 3 |
|---|---|---|---|---|---|
| Content of Allyl- | 0 | 0 | 0 | 0 | 0 |
| (meth) acrylamide | 1 | 200 | 0 | 0 | 0 |
| (ppm) | 3 | 800 | 3 | 5 | 4 |
|  | 6 | 1400 | 7 | 10 | 9 |
| Color (APHA) | 0 | 100 | 100 | 100 | 100 |
|  | 1 | >500 | 100 | 100 | 100 |
|  | 3 | >>500 | 100 | 200 | 100 |
|  | 6 | >>500 | 300 | 400 | 250 |
| Double Bond | 0 | 99.3 | 99.3 | 99.3 | 99.0 |
| Percentage (%) | 1 | 98.1 | 99.2 | 99.3 | 99.1 |
|  | 3 | 97.6 | 99.4 | 99.1 | 98.9 |
|  | 6 | 96.9 | 99.3 | 99.2 | 98.9 |

We claim:

1. A composition having improved storageability, consisting essentially of an N,N-dialkylaminoalkyl(meth)acrylamide of the following formula (II) and an N,N-dialkylhydroxylamine of the following formula (I) in an amount of from 10 to 10,000 ppm:

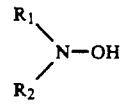

where $R_1$ and $R_2$ each independently represent an alkyl group having from 1 to 4 carbon atoms;

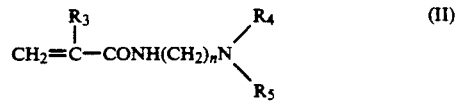

where $R_3$ represents a hydrogen atom or a methyl group; $R_4$ and $R_5$ each independently represent an alkyl group having from 1 to 4 carbon atoms; and n represents an integer of from 2 to 4.

2. The composition as claimed in claim 1, wherein the N,N-dialkylaminoalkyl(meth)acrylamide of the general formula (II) is N,N-dimethylaminopropyl(meth)acrylamide.

3. The composition of claim 1, wherein said N,N-dialkylhydroxylamine is present in an amount of from 10 to 5,000 ppm.

4. The composition of claim 1, wherein said N,N-dialkylhydroxylamine is present in an amount of 300 ppm.

* * * * *